(12) United States Patent
Postolov et al.

(10) Patent No.: US 8,233,699 B2
(45) Date of Patent: Jul. 31, 2012

(54) INSPECTION SYSTEM AND A METHOD FOR DETECTING DEFECTS BASED UPON A REFERENCE FRAME

(75) Inventors: Yuri Postolov, Afula (IL); Menachem Regensburger, Shimshit (IL)

(73) Assignee: Camtek Ltd., Migdal Haemek, IL (US)

( * ) Notice: Subject to any disclaimer, the term of this patent is extended or adjusted under 35 U.S.C. 154(b) by 585 days.

(21) Appl. No.: 12/064,357

(22) PCT Filed: Aug. 29, 2006

(86) PCT No.: PCT/IL2006/000995
§ 371 (c)(1),
(2), (4) Date: Jun. 8, 2009

(87) PCT Pub. No.: WO2007/026350
PCT Pub. Date: Mar. 8, 2007

(65) Prior Publication Data
US 2009/0304260 A1    Dec. 10, 2009

Related U.S. Application Data

(60) Provisional application No. 60/712,142, filed on Aug. 30, 2005, provisional application No. 60/712,143, filed on Aug. 30, 2005, provisional application No. 60/712,144, filed on Aug. 30, 2005.

(51) Int. Cl.
*G06K 9/00* (2006.01)
(52) U.S. Cl. .................. 382/149; 382/141; 382/145
(58) Field of Classification Search .................. None
See application file for complete search history.

(56) References Cited

U.S. PATENT DOCUMENTS

| | | | |
|---|---|---|---|
| 5,495,535 A * | 2/1996 | Smilansky et al. | 382/145 |
| 6,678,404 B1 * | 1/2004 | Lee et al. | 382/155 |
| 6,690,482 B1 * | 2/2004 | Toyoda et al. | 358/1.2 |
| 6,826,298 B1 * | 11/2004 | O'Dell et al. | 382/149 |
| 7,421,110 B2 * | 9/2008 | Nakano et al. | 382/145 |

* cited by examiner

*Primary Examiner* — Jason M Repko
*Assistant Examiner* — Siamak Harandi
(74) *Attorney, Agent, or Firm* — Reches Patents

(57) ABSTRACT

A wafer inspection system and a method for inspecting a wafer. The method includes: acquiring multiple frames that cover a first area that comprises a die and a first surrounding area that surrounds the die; wherein the frames partially overlap to provide overlap areas; and processing a sequence of decomposed images of overlap areas such as to align mutually misaligned frames and generating a die reference image.

8 Claims, 10 Drawing Sheets

INSPECTION SYSTEM AND A METHOD FOR DETECTING DEFECTS BASED UPON A REFERENCE FRAME

RELATED APPLICATIONS

This application claims the priority of U.S. provisional patent Ser. No. 60/712,144, titled "Wafer Mapping and Die Alignment for Post Diced Wafer with Non Linear Distortion of Dice", U.S. provisional patent Ser. No. 60/712,143, titled "Automatic die-model creation and wafer mapping for on-line wafer inspection and random retrieval of die-model data" and U.S. provisional patent Ser. No. 60/712,142, titled "Automatic Visual Inspection of Post Diced Wafer Placed on a Grid", all filed on 30 Aug. 2005.

FIELD OF THE INVENTION

This application relates to a wafer inspection system and methods for inspecting wafers.

BACKGROUND OF THE INVENTION

Integrated circuits are manufactured by a highly complex and costly manufacturing process. During the first stages of this process a wafer is formed. A wafer includes multiple dice that are parallel to each other and are arranged in an ordered array.

FIG. 1 illustrates rectangular-shaped dice that are arranged in columns and rows and are separated by scribe lines. The wafer 11 is characterized by a die X-axis pitch 26 and a die Y-axis pitch 28. Referring to FIG. 1, wafer 11 includes multiple dice 12(0,0)-12(k,j) that are collectively denoted 12. FIG. 1 also illustrates a global coordinate system 20 that includes X-axis 22 and Y-axis 24. The dice are arranged in parallel to these imaginary axes and are aligned with global coordinate system 20.

Wafers are inspected for defects. The inspection can involve comparing between a die and a reference die. The following patents, all being incorporated herein by reference, illustrate various wafer inspection devices and methods as well as registration and alignment methods: U.S. Pat. No. 5,610,102 of Gardopee et al., U.S. Pat. No. 6,021,380 of Fredriksen et al., U.S. Pat. No. 6,937,753 of O'Dell et al., and U.S. Pat. No. 6,324,298 of O'Dell et al., and U.S. Pat. No. 4,981,529 of Tsujita.

In various wafer inspection systems the image processing is applied "off-line". Typically, multiple frames that cover a die are acquired, the location of the die is provided to a scanner that in turn adjusts the scanning pattern such as to align the acquired frames with the dice, and after the scanning process is completed a die to die comparison is preformed.

There is a need to provide an efficient inspection system that can inspect wafers and a method for inspecting wafers.

SUMMARY OF THE INVENTION

A method for inspecting a wafer, the method includes: acquiring multiple frames that cover a first area that comprises a die and a first surrounding area that surrounds the die; wherein the frames partially overlap to provide overlap areas; and processing a sequence of decomposed images of overlap areas such as to align mutually misaligned frames and generating a die reference image.

A method for detecting defects; the method includes: acquiring an acquired frame that comprises portions of multiple dice images; generating a reference frame that differs from a die image, in response to acquired frame spatial information and in response to a reference die image; and comparing between multiple pixels of the acquired frame and multiple corresponding pixels of the reference frame to locate defects.

An inspection system, the system includes: an image acquisition unit adapted to acquire multiple frames, according to a predefined frame acquisition scheme, of a first area that comprises a die and a first surrounding area that surrounds the die; wherein the frames partially overlap to provide overlap areas; and a processor, adapted to process a sequence of decomposed images of overlap areas such as to align mutually misaligned frames and generating a die reference image.

An inspection system, the system includes: a frame acquisition unit adapted to acquire an acquired frame that comprises portions of multiple dice images; and a processor adapted to generate a reference frame that differs from a die image, in response to acquired frame spatial information and in response to a reference die image; and to compare between multiple pixels of the acquired frame and multiple corresponding pixels of the reference frame to locate defects.

BRIEF DESCRIPTION OF THE DRAWINGS

The present invention will be understood and appreciated more fully from the following detailed description taken in conjunction with the drawings in which.

DETAILED DESCRIPTION OF THE DRAWINGS

Various embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Multiple frames are acquired according to a predefined frame acquisition scheme that defines one or more scanning patterns. The method does not require stopping the scanning process in order to adjust the scanning pattern to the location of a die, neither requires to scan all dice of a wafer in order to locate the best die. Conveniently, a reference die image is generated and stored. Portions of the reference die image and retrieved in order to provide a reference frame that is reconstructed in response to a location of acquired frames that are compared to the reference frame in order to detect defects.

In addition, the scanning pattern can start at any location of the wafer, and not necessarily start from a predefined location such as the upper left end of the wafer or of a die. By applying frame comparison and not die to die comparison, defects can be detected by comparing acquired frames that may not be aligned to the borders of a die.

According to an embodiment of the invention the predefined frame acquisition scheme includes defining a certain scanning pattern that is not altered during the frame based comparison. Scanning patterns can include rater scan patterns but this is not necessarily so.

Figure 1:
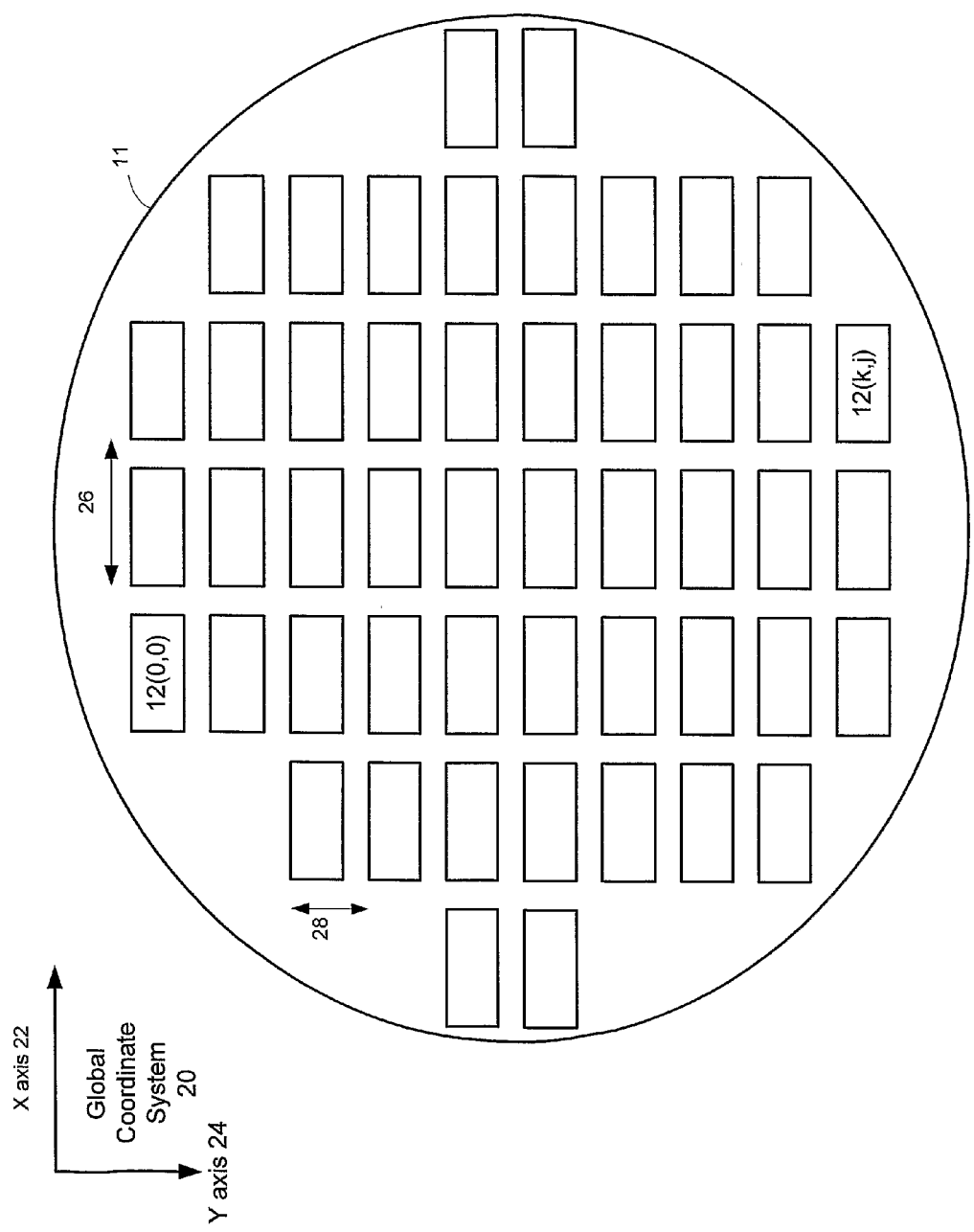
FIG. 1 illustrates a prior art wafer.
Figure 2:
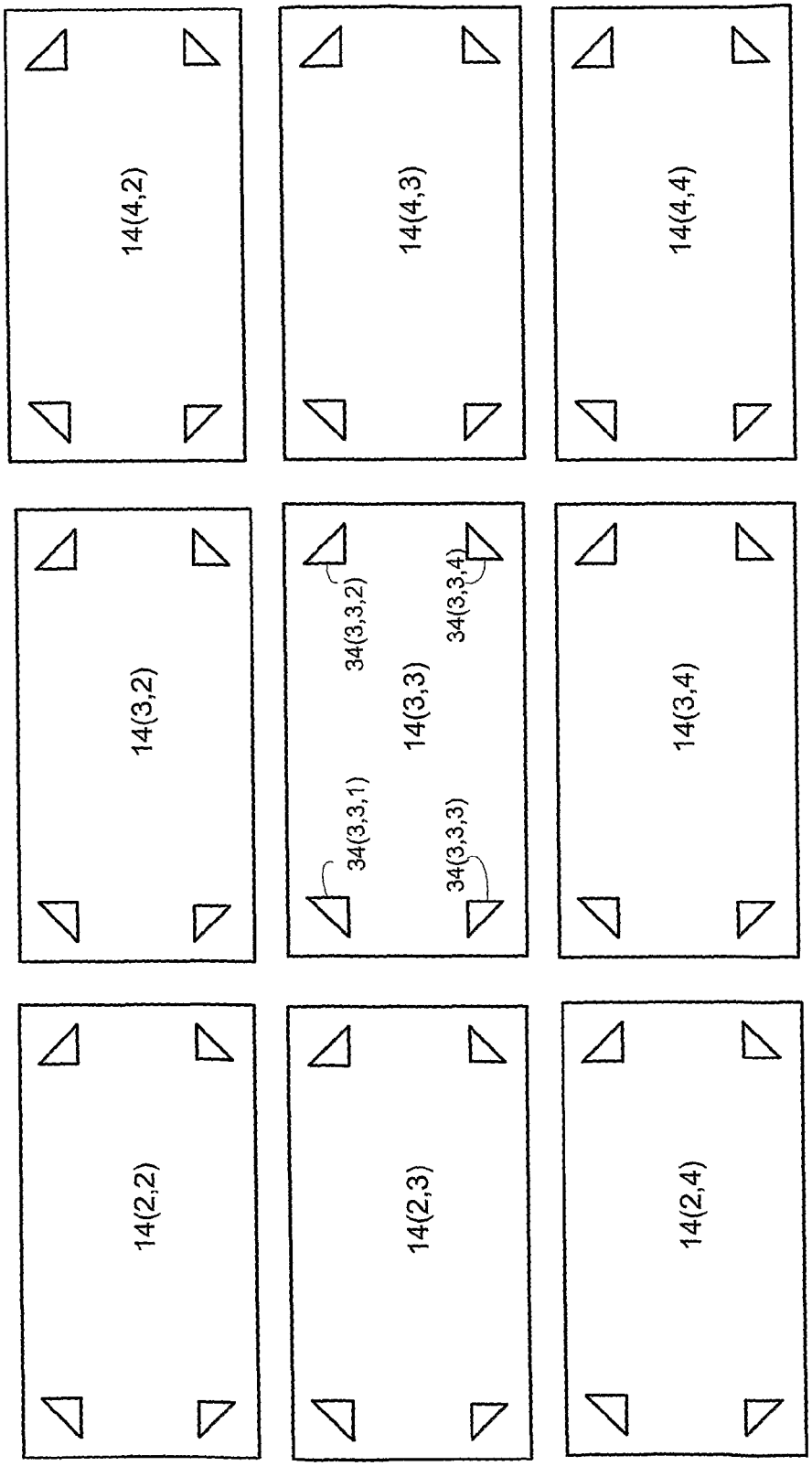
FIG. 2 illustrates multiple dice that include multiple unique features.

FIG. 2 illustrates multiple dice 14(2,2)-14(4,4) that include multiple unique features.

Each die out of dice 14(2,2)-14(4,4) is illustrated as including four unique features. For example die 14(3,3) has three rectangular shaped unique features 34(3,3,1)-34(3,3,4) that are positioned near the corners of die 14(3,3).

The dice are parallel to each other but can be misaligned (as illustrated in FIG. 2) to global coordinate system 20. The misalignment can result from an undesired rotation of a wafer in relation to a stage that can move the wafer along two imaginary axes of the global coordinate system 20.

Figure 3:
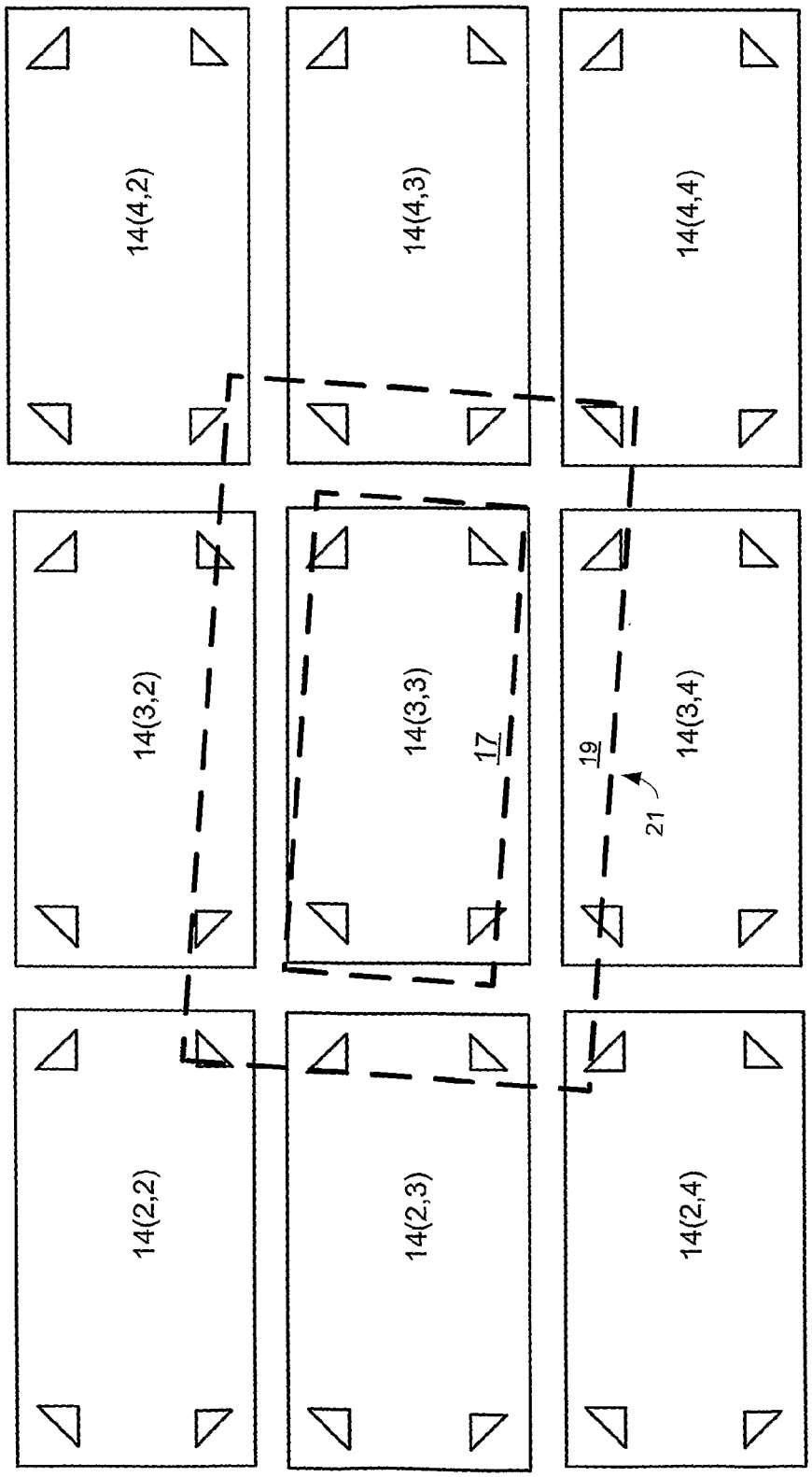
FIG. 3 illustrates multiple dice and a first area according to an embodiment of the invention.

FIG. 3 illustrates multiple dice 14(2,2)-14(4,4) and first area 21 according to an embodiment of the invention.

First area 21 includes a first surrounding area 19 and a rectangular area 17 that is defined by a user. Rectangular area 17 can be defined by the upper left corner of die 14(3,3) and the lower right corner of die 14(3,3). It is noted that first surrounding area 19 can be defined as the area that surrounds die image 14(3,3).

Figure 4:
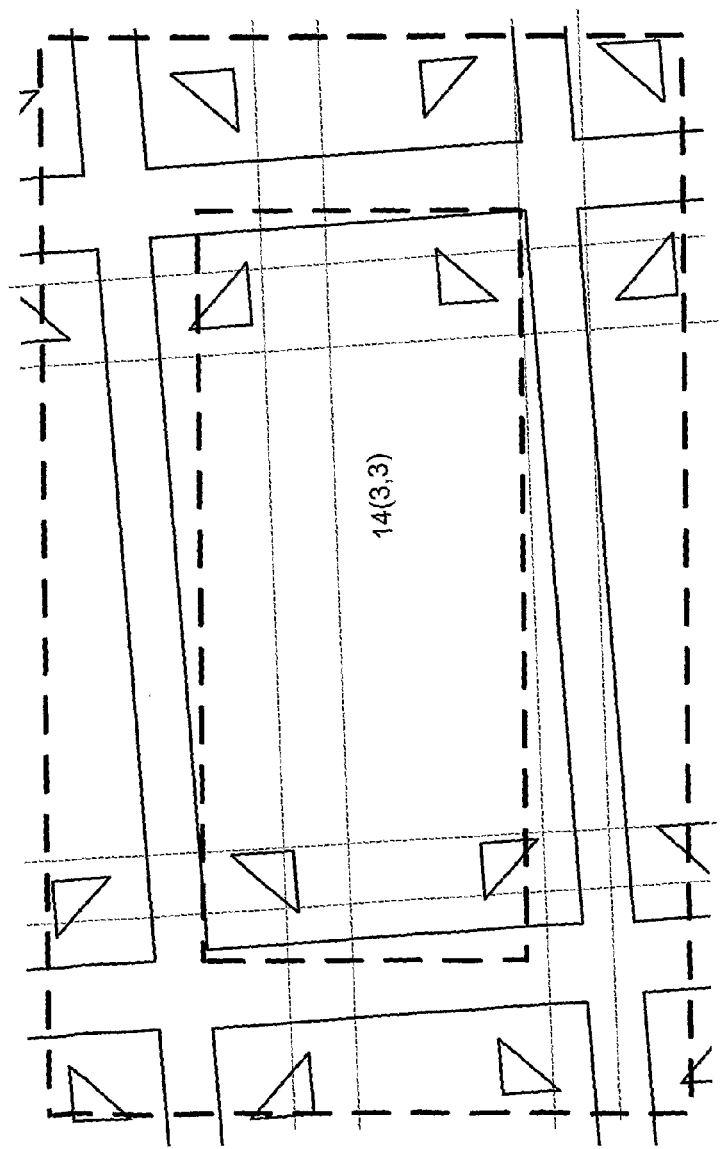
FIG. 4 illustrates multiple frames that cover the first area according to an embodiment of the invention.

FIG. 4 illustrates multiple frames that cover first area 21 according to an embodiment of the invention. The different rectangular frames partially overlap and are illustrated by dashed lines. Each frame is smaller than die 14(3,3).

It is noted that the frame comparison method can be applied in cases where a single frame include more than a single die image.

Figure 5:
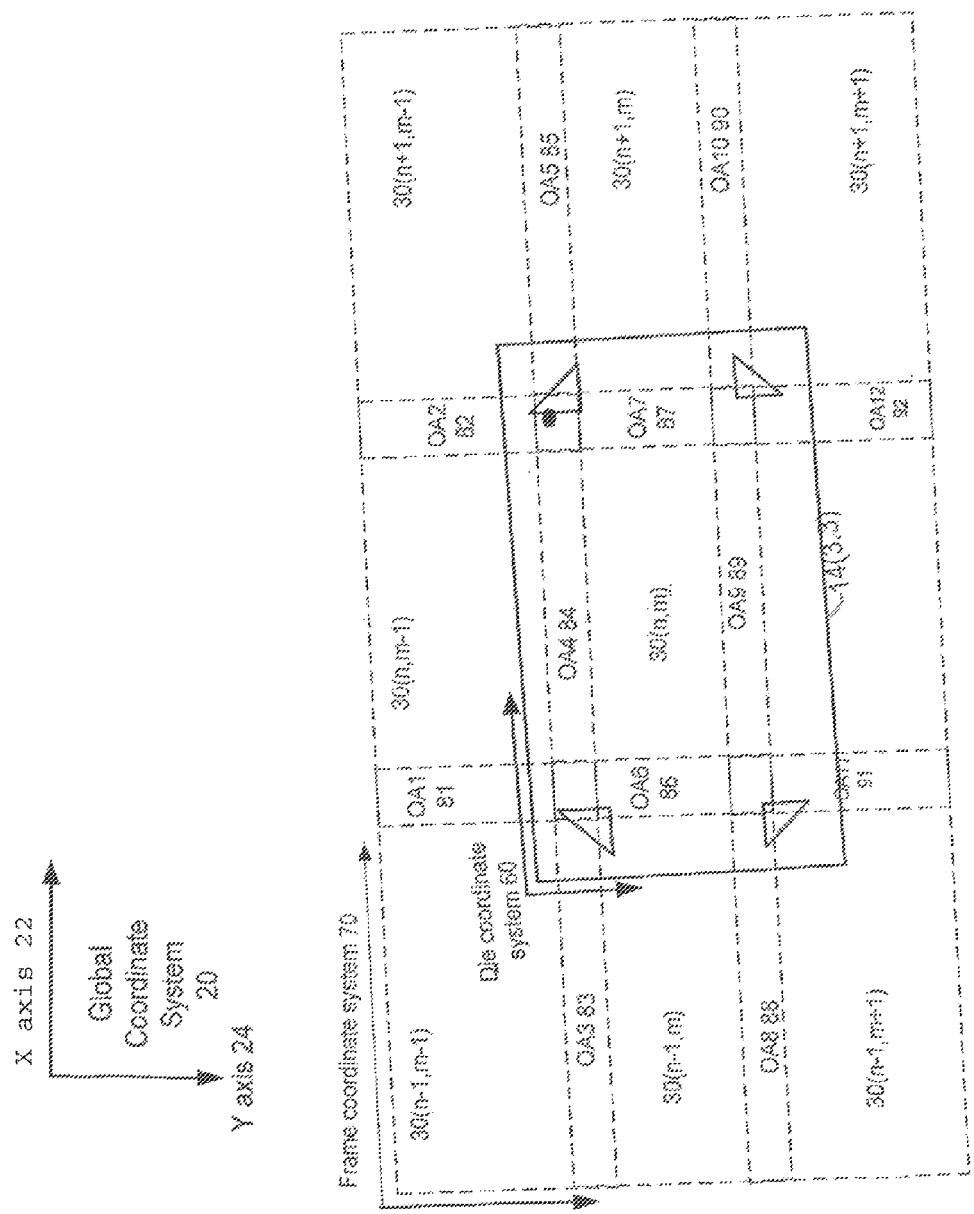
FIG. 5 illustrates an image of a die, multiple frames and three coordinate systems, according to an embodiment of the invention.

FIG. 5 illustrates multiple frames 30(n−1,m)-30(n+1, m+2), die 14(3,3), first area 21, overlap areas 81-92 and three coordinate systems according to an embodiment of the invention.

It is assumed that die 14(3,3) belongs to an un-sawn wafer. Accordingly, the dice of this wafer are parallel to each other. If an inspected wafer was sawn then dice were mutually misaligned and a coordinate system of one die could not have been used to efficiently describe another (unparallel) die. In this case the wafer inspection process should include determining the angular relationships between different die coordinate systems.

The image of die 14(3,3) includes multiple pixels. The location of different pixels is defined in relation to die coordinate system 60.

FIG. 5 also illustrates multiple frames (acquired images) that are acquired by a frame acquisition unit. These frames should be aligned to each other but in practice they are slightly misaligned.

The frames are also not aligned with global coordinate system 20. This misalignment can result from mechanical inaccuracies of the inspection system as well as from other reasons such as misplacement of the wafer of the mechanical stage that translated the wafer, optical path aberrations, sensor orientation and the like.

FIG. 5 illustrates a set of 3×3 frames 30(n−1,m−1)-30(n+1, m+1) that cover a die 14(3,3) and its proximate vicinity.

It is noted that a die usually includes multiple unique features and that it is expected that most overlap area will include multiple unique features. For simplicity of explanation only four unique features per die were shown, although a die usually includes a large number of unique features, most of them are much smaller than unique features 34(3,3,1)-34(3,3,4). Unique features of different sized can be detected in images of overlap area that are characterized by a different decomposition level.

The frames overlap thus defining overlap areas. An overlap area is an area that is included in two adjacent frames. Frame 30(n−1,m−1) and frame 30(n,m−1) define overlap area OVA1 81. Frame 30(n,m−1) and frame 30(n+,m−1) define overlap area OVA2 82. Frame 30(n−1,m−1) and frame 30(n−1,m) define overlap area OVA3 83. Frame 30(n,m−1) and frame 30(n,m) define overlap area OVA4 84. Frame 30(n+1,m−1) and frame 30(n+1,m) define overlap area OVA5 85. Frame 30(n−1,m) and frame 30(n,m) define overlap area OVA6 86. Frame 30(n, m) and frame 30(n+1,m) define overlap area OVA7 87. Frame 30(n−1,m) and frame 30(n,m+1) define overlap area OVA8 88. Frame 30(n, m) and frame 30(n,m+1) define overlap area OVA9 89. Frame 30(n+1,m) and frame 30(n+1,m+1) define overlap area OVA10 90. Frame 30(n−1, m+1) and frame 30(n,m+1) define overlap area OVA11 91. Frame 30(n,m+1) and frame 30(n+1,m+1) define overlap area OVA12 92.

Unique feature 34(3,3,1) is partially included in overlap areas OA1 81 and OA3 83, and is partially included in frames 30(n−1,m−1), 30(n,m−1), 30(n−1,m) and 30(n,m). Unique feature 34(3,3,2) is partially included in overlap areas OA2 82 and OA5 85, is partially included in frames 30(n,m−1), 30(n, m) and 30(n+1,m) and is fully included in frame 30(n+1,m−1). Unique feature 34(3,3,3) is partially included in overlap areas OA8 88 and OA11 91, is partially included in frames 30(n,m+1), 30(n,m) and 30(n−1,m) and is fully included in frame 30(n−1,m+1). Unique feature 34(3,3,4) is partially included in overlap areas OA7 87, OA9 89 and OA10 90, is partially included in frames 30(n, m), 30(n,m+1) and 30(n+1,m) and is fully included in frame 30 (n+1,m+1).

If an overlap area includes more or multiple unique features then the location of this unique features in each of the overlapping frames that define the overlap area can assist in defining the relative translation between the overlapping frames and accordingly can assist in aligning these overlapping frames in order to generate a single die reference image.

In order to speed up the frame alignment process, and especially for allowing on-the-fly (during frame acquisition) frame alignment, the frame alignment process includes processing decomposed images of the overlap areas. Referring to the example set forth in FIG. 5, decompressed images of overlap areas OA1-OA12 81-92 are generated.

The decomposition can include applying a Gaussian pyramid, a Laplacian pyramid or another fast decomposition scheme in order to generate a set of decomposed images of the overlap area, whereas the different images are characterized by different decomposition level. Various decomposition technique are illustrated in U.S. Pat. No. 6,005,978 of Garakani, U.S. Pat. No. 6,678,404 of Lee et al and PCT patent application publication serial number WO 99/01985 of Lee et al., all being incorporated herein by reference.

Conveniently, unique features are searched in the most composed image of the overlap area. If one or more unique features are located then their exact location is defined by analyzing less decomposed images (up to the non-composed image of the overlap area) of the overlap area, and especially concentrating on the vicinity of previously located unique features. If the overlap area does not include a unique feature then the alignment between two adjacent frames can be estimated in response to misalignment of other adjacent frames. The estimation can include interpolation.

Figure 6:
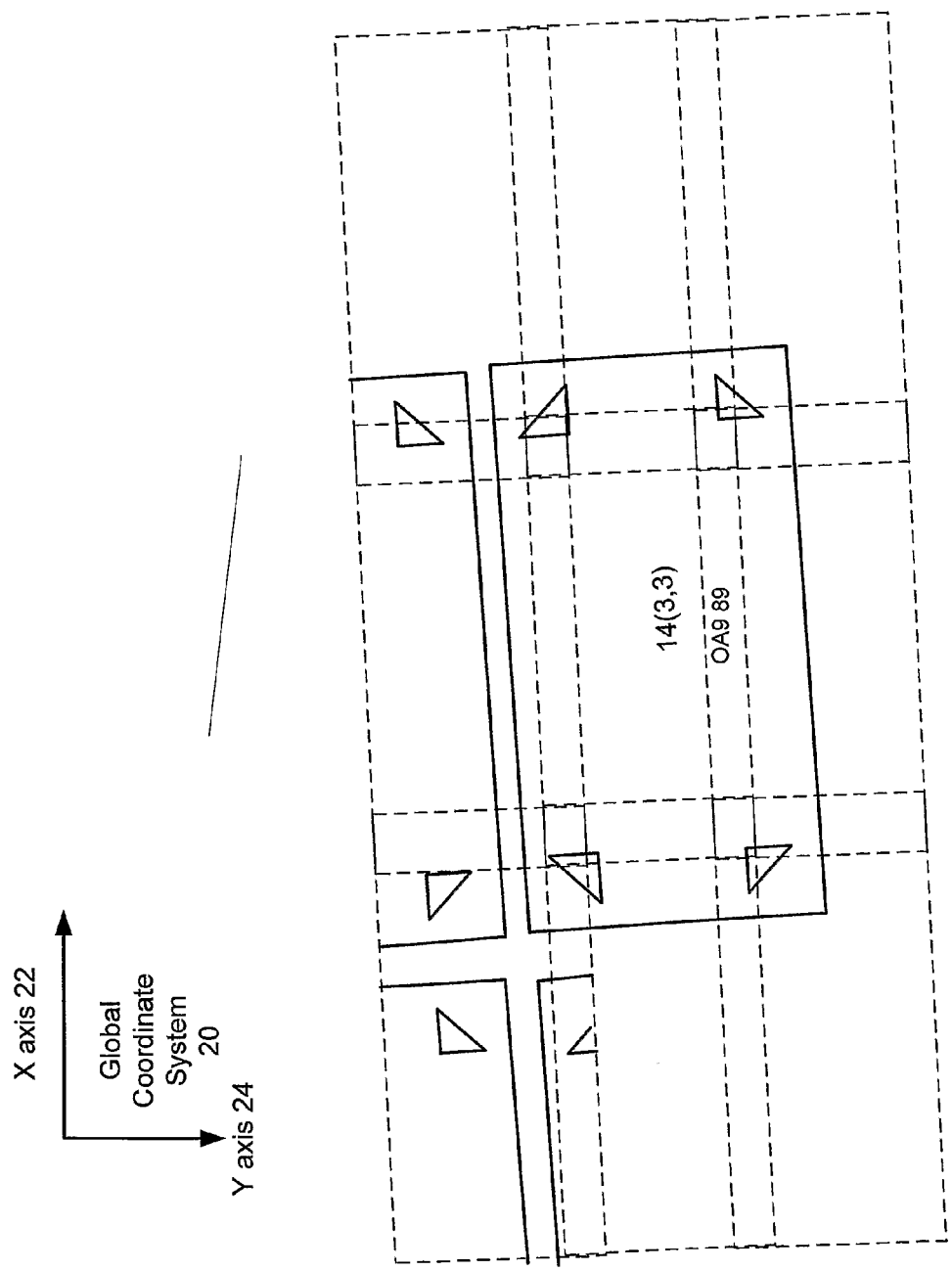
FIG. 6 illustrates multiple frames, die image and various die image portions, according to an embodiment of the invention.

FIG. 6 illustrates multiple frames, die image and various die image portions, according to an embodiment of the invention.

FIG. 6 illustrates an image of die 14(3,3) as well as frame 30(n−1, m−1) that includes portion 14'(2,2) of the image of die 14(2,2), portion 14'(3,2) of the image of die 14(3,2), and portion 14'(2,3) of the image of die 14(2,3). Frame 30(n−1, m−1) also includes portion 14'(3,3) of the image of die 14(3, 3).

Figure 7:
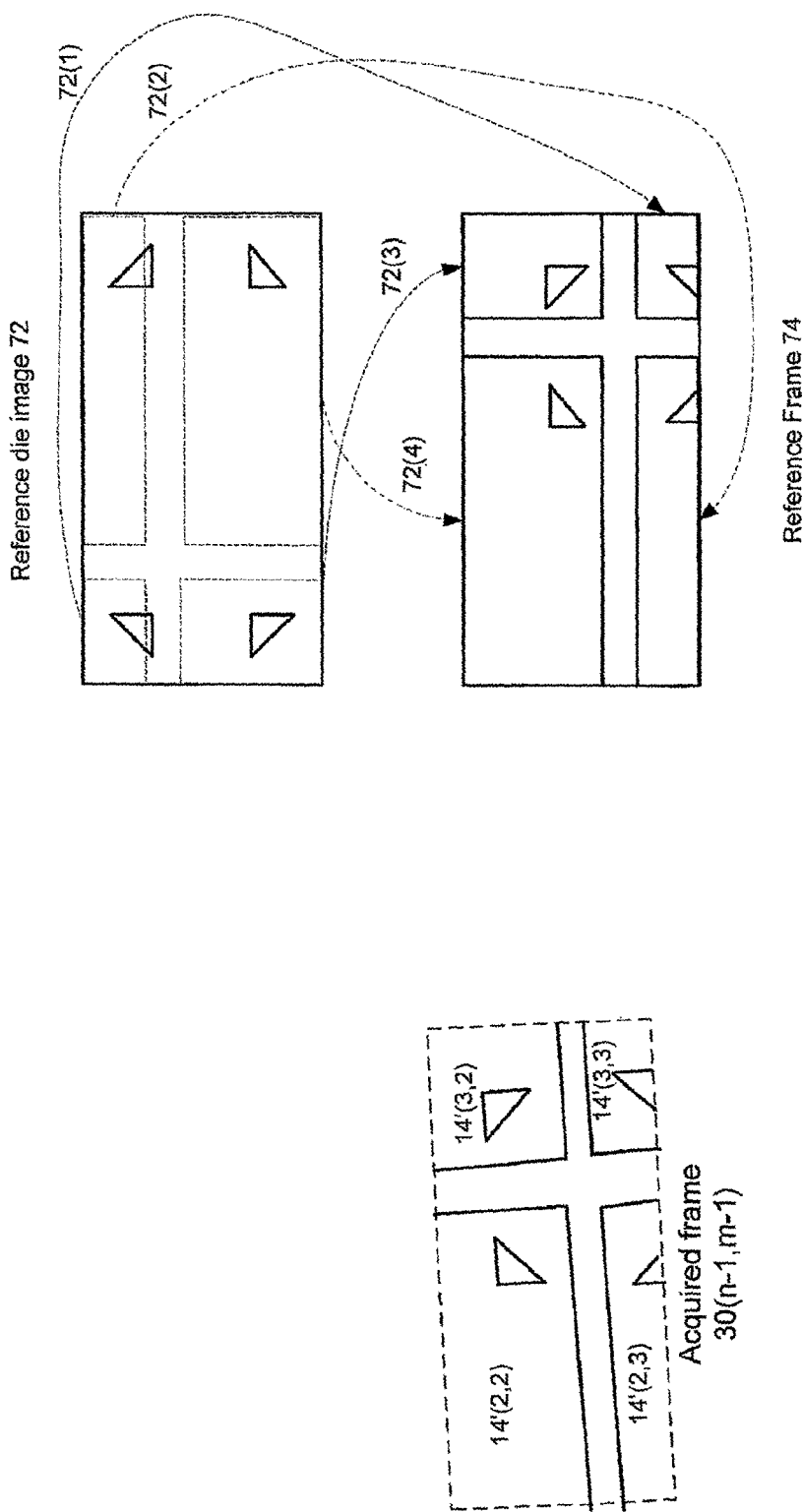
FIG. 7 illustrates an acquired frame, a reference die image and a reference frame according to an embodiment of the invention.

FIG. 7 illustrates acquired frame 30(n−1, m−1), reference die image 72 and a reference frame 74 according to an embodiment of the invention.

Reference die image 72 includes an image of a die without its surroundings. It is conveniently aligned to a global coordinate system 20. Reference die image 72 was reconstructed from multiple frames that were merged to a single image, after being aligned. Pixels of the merged image that do not belong to a die were omitted from the die image, thus leaving only pixels that represent a single die. For example, assuming that the image of die 14(3,3) can be reconstructed from frames 30(n−1, m−1)-30(n+1, m+1) then pixels that belong to these frames that do not belong to the image of die 14(3,3) are omitted to provide reference die image 72. The reference die image 72 is also aligned with global coordinate system 20, although this is not necessarily so. Reference die image can be reconstructed on line, off line, can be represent multiple previously imaged dice, can be generated by applying statistical analysis of previously imaged dice, and the like. The reference die image can be generated by another inspection system, can be retrieved from a database. Conveniently it is generated on the fly, and is used for comparison to frames acquired during a single scanning pattern of the inspection system.

Acquired frame 30(n−1, m−1) includes portions 14'(2,2)-14'(3,3). The approximate location of acquired frame 30(n−1,m−1) is known, as the frame acquisition process includes tracking after the position of acquired frames. By processing a portion of the acquired frame (especially locating unique features and determining their location) the exact location of frame 30(n−1, m−1) can be determined and the reference frame can be defined.

Reference frame 74 includes portions 72(1)-72(4) of reference die image 72. The size of each portion as well as its location in the reference frame is determined in view of the estimated portions of die images (for example portions 14,(2, 2)-14'(4,4)) that are included in acquired frame 30(n−1,m−1). The estimated portions of these die images can be estimated in view of the die pitch, die size and the spatial relationship between borders of acquired frame 30(n−1,m−1) and borders of die images (for example images 14(2,2)-14(3,3)) that are at least partially included in the acquired frame.

Conveniently, mathematical operations (such as warp, interpolation) and the like are applied on the acquired frame such as to align the acquired frame with the reference frame.

After this alignment the pixels of the reference frame can be compared to the pixels of the acquired frame in order to detect defects. A defect can be detected by differences between pixels, between pixel groups and the like.

According to another embodiment of the invention the comparison is preceded by applying a frame acquisition process representative conversion on the acquired frame. This conversion represents the illumination and frame acquisition paths of an inspecting system. This conversion can be determined during a wafer inspection system calibration stage (for example illuminating a test target). The conversion compensates for aberrations, sensor un-uniformities, sensor saturation level, as well as other linear or non-linear phenomena that can affect the intensity level of an acquired pixel. This conversion can improve the accuracy of defect detection.

Figure 8:
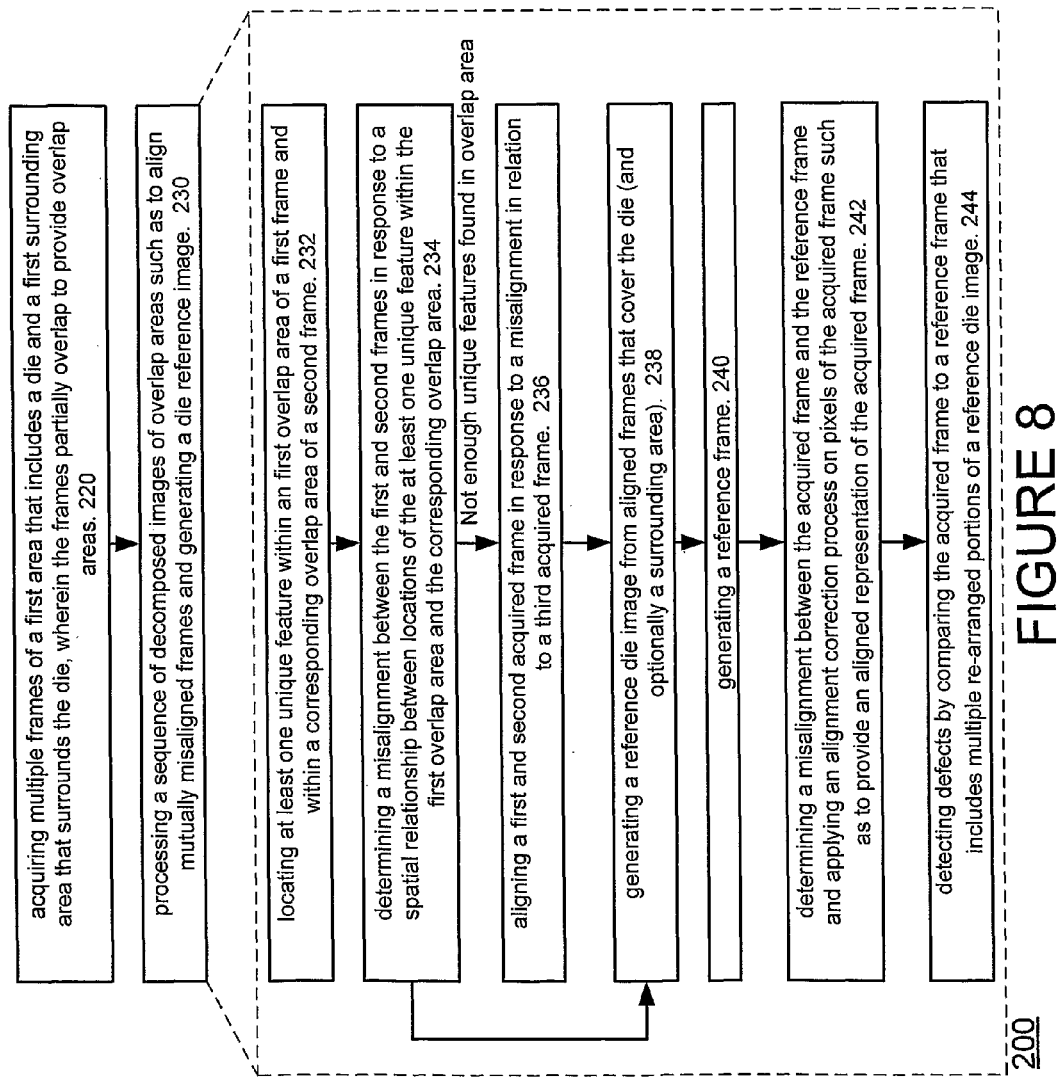
FIG. 8 illustrates a method according to an embodiment of the invention.

FIG. 8 illustrates method 200 for detecting defects, according to an embodiment of the invention.

Method 200 starts by stage 220 of acquiring multiple frames that provide an image of a first area that includes a die and a first surrounding area that surrounds the die, wherein the frames partially overlap to provide overlap areas.

The size of the first area can be defined by a user or calculated in response to the size of the die and a frame acquisition uncertainty factor. The size of the surrounding area is designed such as to guarantee that a die will be covered, regardless of possible frame acquisition inaccuracies, wafer and/or die rotation or misalignment and the like.

Stage 220 is followed by stage 230 of processing a sequence of decomposed images of overlap areas such as to align mutually misaligned frame and generating a die reference image.

Conveniently, unique features can be located by applying normalized correlation or geometric hashing. Geometric hashing is described in the following articles and patents, all being incorporated herein by reference: "Rehashing for Bayesian Geometric Hashing", M. Lifshits, I. Blayvas, R. Goldenberg and E. Rivlin, Proceedings of the 17$^{th}$ international conference on pattern recognition (ICPR'04), "Geometric Hashing: An Overview, H. J. Wolfson and I. Rigoutsos, IEEE Computational Science & Engineering, 1997 IEEE, U.S. Pat. No. 6,941,016 of Wagman et al., U.S. Pat. No. 7,027,651 of Simon et al., and U.S. Pat. No. 6,993,192 of Silver.

Conveniently, stage 230 further includes processing non-decomposed images of overlap areas and in response to a content of the non-decomposed images and decomposed images of the overlap areas aligning mutually misaligned images.

Conveniently, stage 230 includes stage 232 of locating at least one unique feature within a first overlap area of a first frame and within a corresponding overlap area of a second frame. Stage 232 is followed by stage 234 of determining a misalignment between the first and second frames in response to a spatial relationship between locations of the at least one unique feature within the first overlap area and the corresponding overlap area. It is noted that stages 232 and 234 can be executed on decomposed images of these area. Conveniently the first iteration of stage 232 and 234 involves processing the most de-composed images of the overlap area while additional iterations involve processing less decomposed images. Once a unique feature is found the processing of less decomposed images can concentrate around previously located unique features.

Conveniently, stage 234 is followed (once the iterations of stages 232 and 243 end) by stage 236 of aligning a first and second frames in response to a misalignment in relation to a third frame. This can occur if an overlap area does not include any (or enough) unique features.

Stage 236 is followed by stage 238 of generating a reference die image from aligned frames that cover the die (and optionally a surrounding area).

Conveniently, stage 238 is followed by stage 240 of generating a reference frame. If, for example, a frame includes portions of multiple dice images then stage 240 includes generating a reference frame that differs from a die image, in response to acquired image spatial information and in response to a reference die image. Referring to the example set forth in FIG. 7, reference frame 74 is generated by selecting portions 72(1)-72(4) that correspond to image portions 14'(2,2)-14'(3,3) within acquired frame 30(n−1, m−1). It is noted that a reference frame can include a portion of a die, a single die and one or more dice portions, multiple dice portions and the like. The reference frame differs from an image of a die. It is noted that the frame based comparison allows to compare frames that were acquired at arbitrary locations of the wafer, and they do not require to align the scanning pattern to the exact location of a die. Thus, occasionally the reference frame can equal a die image, but usually this is not the case.

Stage 240 is followed by stage 242 of determining a misalignment between the acquired frame and the reference frame and applying an alignment correction process on pixels of the acquired frame such as to provide an aligned representation of the acquired frame.

Stage 242 is followed by stage 244 of detecting defects by comparing the acquired frame to a reference frame that includes multiple re-arranged portions of a reference die image.

Conveniently, stage 230 includes performing an image acquisition process representative conversion of acquired images.

Figure 9:
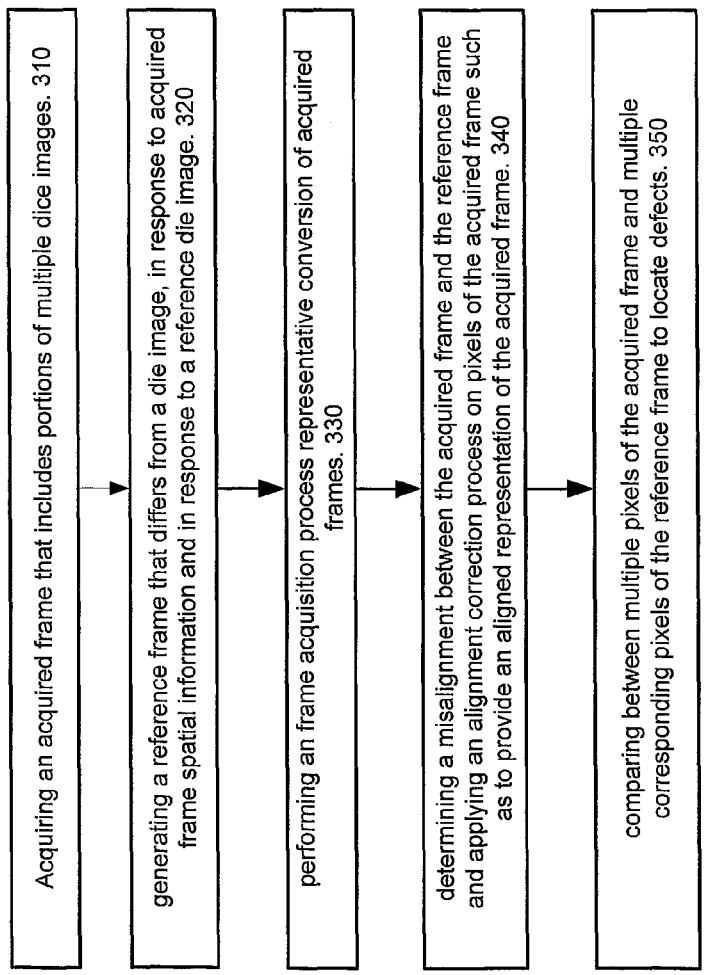
FIG. 9 illustrates a method according to another embodiment of the invention.

FIG. 9 illustrates method 300, according to an embodiment of the invention.

Method 300 starts by stage 310 of acquiring an acquired frame that includes portions of multiple dice images.

Stage 310 is followed by stage 320 of generating a reference frame that differs from a die image, in response to acquired image spatial information and in response to a reference die image.

Stage 320 is followed by stage 330 of performing an image acquisition process representative conversion of acquired images.

Stage 330 is followed by stage 340 of determining a misalignment between the acquired frame and the reference frame and applying an alignment correction process on pixels of the acquired frame such as to provide an aligned representation of the acquired frame.

Stage 340 is followed by stage 350 of comparing between multiple pixels of the acquired frame and multiple corresponding pixels of the reference frame to locate defects.

Figure 10:
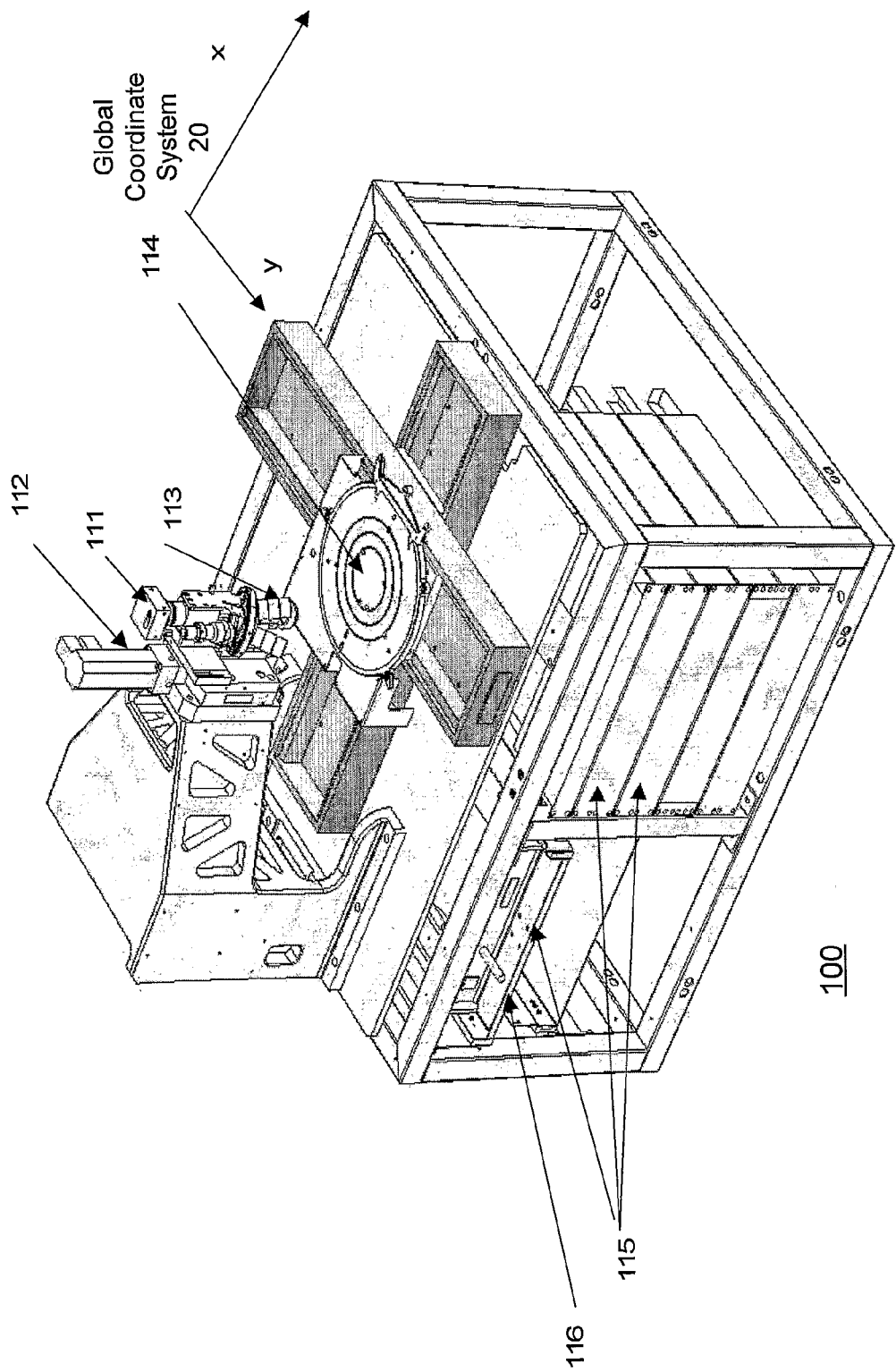
FIG. 10 illustrates a wafer inspection system, according to an embodiment of the invention.

FIG. 10 illustrate system 100 according to an embodiment of the invention. System 100 includes image acquisition unit 111, processor 115, illuminator 112, optics 113, a mechanical stage such as X-Y table 114 and storage unit 116.

System 100 can define or receive a predefined image acquisition scheme and accordingly scan the diced wafer while acquiring images.

X-Y table 114 is adapted to introduce a continuous mechanical translation between the diced wafer and the image acquisition unit.

Image acquisition unit 111 can include one or more detectors that can acquire an image of an area illuminated by illuminator 112. Optics 13 may serve the illumination of a diced wafer (placed on X-Y table 114) as well as serve for collecting light and directing it towards image acquisition unit 111. Storage unit 116 stored acquired images and is accessible by processor 115. It is noted that the detection signals from image acquisition unit 111 can be processed by processor 115 in order to provide frames.

The wafer can be illuminated by overlapping strobes of light that forming overlapping images of frames.

The motion of X-Y table 114 is managed electronically by high precision control system, this enables to correlate the exact location of each pixel in the scanned object (image) in relation to global coordinate system 20.

Conveniently, image acquisition unit 112 is adapted to acquire multiple frames, according to a predefined image acquisition scheme, of a first area that includes a die and a first surrounding area that surrounds the die. The frames partially overlap to provide overlap areas.

Processor 115 is adapted to process a sequence of decomposed images of overlap areas such as to align mutually misaligned frames and generating a die reference image.

Conveniently processor 115 is adapted to perform at least one of the following operations, or a combination thereof: (i) process non-decomposed images of overlap areas and in response to a content of the non-decomposed images and decomposed images of the overlap areas align mutually misaligned images, (ii) locate at least one unique feature within an first overlap area of a first frame and within a corresponding overlap area of a second frame and determine a misalignment between the first and second images in response to a spatial relationship between locations of the at least one unique feature within the first overlap area and the corresponding overlap area, (iii) align a first and second frame image in response to a misalignment in relation to a third frame image, (iv) detect defects by comparing the acquired frame to a reference frame that includes multiple portions of a reference die image, if the acquired frame is representative of multiple dice images portions, (v) determine a misalignment between the acquired frame and the reference frame and apply an alignment correction process on pixels of the acquired frame such as to provide an aligned representation of the acquired frame, (vi) perform an image acquisition process representative conversion of acquired images, (vii) generate the reference frame from at least one portions of a reference die image; wherein the processor selects the portions in response to a location of the acquired frame, (viii) determine a spatial characteristic of the first surrounding area in response to uncertainty in an image acquisition process.

Additionally or alternatively, image acquisition unit 112 is adapted to acquire an acquired frame that comprises portions of multiple dice images and processor 115 is adapted to perform at least one of the following operations or a combination thereof: (i) generate a reference frame that differs from a die image, in response to acquired image spatial information and in response to a reference die image; (ii) compare between multiple pixels of the acquired frame and multiple corresponding pixels of the reference frame to locate defects, (iii) determine a misalignment between the acquired frame and the reference frame and apply an alignment correction process on pixels of the acquired frame such as to provide an aligned representation of the acquired frame, (iv) perform an image acquisition process representative conversion of acquired images, (v) generate the reference frame from multiple portions of a reference die image; wherein the portions are selected in response to a location of the acquired frame.

It is noted that memory unit 116 can also store images of the reference dice as well as information relating to the acquired frames.

Image acquisition unit 111 can include one or more line sensors, point sensors, two dimension sensor arrays and the like. Illuminator 112 can include a laser source a lamp, can provide light pulses or continuous illumination, can illuminate a spot or illuminate an area. Illuminator 112 is illustrated as bright field illuminator but system 100 can apply, additionally or alternatively, dark filed illumination.

Processor 115 can also control the operation of the various components of system 100 but this is not necessarily so and system 100 can include one or other controllers that control the operation of system 100.

Conveniently, processor 115 can include multiple components that can operate in parallel in order to increase the processing speed of system 100. These components can perform the same function or different functions.

Conveniently, storage unit 116 may include one or multiple storage components that be accessed serially or in a parallel manner, for speeding to processing speed of system 100. Different storage unit components can store different type of information or the same type of information.

According to various embodiments of the invention the mentioned above methods and inspection system can perform defect detection of diced wafers. Diced wafers are characterized by dice that are not arranged in an orderly manner. Each die can be defined by its own die coordinate system. In this case the generation of a reference frame is preceded by generating a diced wafer map or at least determining the spatial relationships between dice images that can be partially included within an acquired frame.

It is further noted that the mentioned above methods and systems can be adapted to operate with frames that include multiple dice images. In this case a die reference image can be generated without aligning frames.

According to an embodiment of the invention images of adjacent dice are provided, aligned to each other and size characteristics such as die pitch are measured.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

We claim:

1. A method for detecting defects; the method comprises:
   acquiring, by an image acquisition unit and according to a scanning pattern, an acquired frame that comprises portions of multiple dice images;
   generating, by a processor of an inspection system, a reference frame that differs from a die image, in response to acquired frame spatial information and in response to a reference die image; wherein the reference frame comprises re-arranged portions of a reference die image, wherein locations of the portions of the reference die image correspond to locations of the portions of multiple dice images in the acquired frame;
   wherein if an upper right portion of the acquired frame comprises an image of a lower left portion of a first die and a lower right portion of the acquired frame comprises an image of an upper left portion of a second die then the generating comprises generating a reference frame that has an upper right portion that comprises a lower left portion of the reference die image and a lower right portion that comprises an upper left portion of the reference die image;
   comparing, by the processor of the inspection system, between multiple pixels of the acquired frame and multiple corresponding pixels of the reference frame to locate defects.

2. The method according to claim 1 further comprising determining a misalignment between the acquired frame and the reference frame and applying an alignment correction process on pixels of the acquired frame such as to provide an aligned representation of the acquired frame.

3. The method according to claim 1 further comprising performing a frame acquisition process representative conversion of acquired frames.

4. The method according to claim 1 further comprising generating the reference frame from multiple portions of a reference die image; wherein the portions are selected in response to a location of the acquired frame.

5. An inspection system, the system comprises:
   a frame acquisition unit adapted to acquire an acquired frame that comprises portions of dice images; and
   a processor adapted to generate a reference frame that differs from a die image and comprises re-arranged portions of a reference die image, wherein locations of the portions of the reference die image correspond to locations of the portions of multiple dice images in the acquired frame;
   wherein if an upper right portion of the acquired frame comprises an image of a lower left portion of a first die and a lower right portion of the acquired frame comprises an image of a upper left portion of a second die then the generating comprises generating a reference frame that has an upper right portion that comprises a lower left portion of the reference die image and a lower right portion that comprises a upper left portion of the reference die image;
   wherein the processor is adapted to generate the reference frame in response to acquired frame spatial information and in response to the reference die image; and to compare between multiple pixels of the acquired frame and multiple corresponding pixels of the reference frame to locate defects.

6. The system according to claim 5 wherein the processor is adapted to determine a misalignment between the acquired frame and the reference frame and apply an alignment correction process on pixels of the acquired frame such as to provide an aligned representation of the acquired frame.

7. The system according to claim 5 wherein the processor is adapted to perform a frame acquisition process representative conversion of acquired frames.

8. The system according to claim 5, wherein the processor is adapted to generate the reference frame from multiple portions of a reference die image; wherein the portions are selected in response to a location of the acquired frame.

* * * * *